United States Patent [19]

Häussling et al.

[11] Patent Number: 5,821,383
[45] Date of Patent: Oct. 13, 1998

[54] PREPARATION OF (METH) ACRYLIC ESTERS

[75] Inventors: Lukas Häussling, Bad Dürkheim; Ludwig Bernhard, Heppenheim; Wolfgang Reich, Maxdorf; Reinhold Schwalm, Wachenheim; Erich Beck, Ladenburg, all of Germany

[73] Assignee: Basf Aktiengesellschaft, Germany

[21] Appl. No.: 747,762

[22] Filed: Nov. 13, 1996

[30] Foreign Application Priority Data

Nov. 22, 1995 [DE] Germany ............ 195 43 464.1

[51] Int. Cl.⁶ .................................. C07C 69/52
[52] U.S. Cl. ...................... 560/205; 106/287.26
[58] Field of Search ............... 560/205; 106/287.26

[56] References Cited

U.S. PATENT DOCUMENTS 5,258,138  11/1993  Gatechair et al. ............. 560/205

FOREIGN PATENT DOCUMENTS 0 680 985  11/1995  European Pat. Off. .

OTHER PUBLICATIONS

Database WPI, Derwent Publications, AN–94 290862, JP–A–06 219 991, Aug. 9, 1994.

*Primary Examiner*—Paul J. Killos
*Attorney, Agent, or Firm*—Oblon, Spivak, McClelland, Maier & Neustadt, P.C.

[57] ABSTRACT

A process for preparing (meth)acrylic esters by esterifying (meth)acrylic acid with monohydric or polyhydric alcohols comprises adding to the reaction mixture still comprising (meth)acrylic acid corresponding to an acid number of at least 5 mg of KOH per 1 g of reaction mixture at least one amino compound having at least one primary, secondary or tertiary amino group.

6 Claims, No Drawings

PREPARATION OF (METH) ACRYLIC ESTERS

The present invention relates to a process for preparing (meth)acrylic esters..Various processes are known for preparing (meth)acrylic esters. These processes all have in common that excess or unconverted (meth)acrylic acid is removed from the reaction product because of its pungent odor.

In the process of DE-A-2913218, volatiles are removed from (meth)acrylic ester product by blowing in air to the product. EP-A-618187 describes a scrubbing process for removing (meth)acrylic acid. Another possible way of removing residual (meth)acrylic acid is the reaction with epoxies to form epoxyacrylates, known for example from EP-A-127766.

Primary or secondary amino compounds are known to enhance the reactivity of (meth)acrylic esters in radiation curing. According to EP-A-586849 and EP 280222, for example, (meth)acrylic esters are modified with primary or secondary amino compounds for use in radiation-curable coatings.

It is an object of the present invention to provide a process for preparing (meth)acrylic esters without having to effect a substantially complete removal of the excess or unconverted (meth)acrylic acid to obtain (meth)acrylic esters highly suitable for use as or in radiation-curable compositions.

We have found that this object is achieved by a process for preparing (meth)acrylic esters by esterifying (meth) acrylic acid with monohydric or polyhydric alcohols, which comprises adding to the reaction mixture still comprising (meth)acrylic acid corresponding to an acid number of at least 5 mg of KOH per 1 g of reaction mixture at least one amino compound having at least one primary, secondary or tertiary amino group.

The esterification of methacrylic acid or preferably acrylic acid with monohydric or preferably polyhydric alcohols is well known.

Suitable polyhydric alcohols include in particular $C_{2-C10}$ -alka- ne-diols, -triols or -tetrols, for example butanediol, hexane-diol, trimethylolpropane, pentaerythritol.

Also possible are hydroxyl-containing ethers and polyethers or hydroxyl-containing polyesters. Preference is given to ethers, especially polyethers and polyesters containing from 2 to 6, preferably from 2 to 4 and particularly preferably 2 hydroxyl groups.

The molecular weights $M_n$ of the polyesters or polyethers or ethers are preferably within the range from 100 to 4000.

Such hydroxyl-containing polyesters can be prepared, for example, in a conventional manner by esterifying dicarboxylic acids or polycarboxylic acids with diols or polyols. The starting materials for such hydroxyl-containing polyesters are known to those skilled in the art. Preferred dicarboxylic acids are succinic acid, glutaric acid, adipic acid, sebacic acid, o-phthalic acid, their isomers and hydrogenation products and also esterifiable derivatives, such as anhydrides, for example maleic anhydride, or dialkyl esters of the acids mentioned. Suitable polycarboxylic acids and anhydrides are tri- or tetrabasic acids such as trimellitic anhydride or benzenetetracarboxylic acid. Preferred diols are ethylene glycol, 1,2 -propylene glycol, 1,3 -propylene glycol, 1,4 -butanediol, 1,6 -hexanediol, neopen-tylglycol, cyclohexanedimethanol and also polyglycols of the ethylene glycol and propylene glycol type.

Suitable polyols are primarily trimethylolpropane, glycerol or pentaerythritol and also ditrimethylolpropane, sorbitol and di-pentaerythritol.

Suitable diols or polyols also include oxalkylated, for example ethylated or propoxylated, diols or polyols, especially with a degree of alkoxylation of from 0 to 10, based on the respective hydroxyl groups of the diol or polyol.

Hydroxyl-containing polyethers include for example those which can be obtained by known processes by reacting dihydric and/or more highly hydric alcohols with various amounts of ethylene oxide and/or propylene oxide. It is similarly possible to use polymerization products of tetrahydrofuran or butylene oxide.

Preference is given to alkoxylation products of the above-mentioned diols or polyols, especially with a degree of alkoxylation of from 0 to 10, based on the respective hydroxyl groups of the diol or polyol, provided at least 2 ether groups are present in the molecule.

In the esterification, the acrylic acid or methacrylic acid can be used in deficiency or else in large excess, based on the OH groups.

Preference is given to using from 0.7 to 2.0 mol, particularly preferably from 0.9 to 1.5 mol, and especially from 1.0 to 1.5 mol, of acrylic acid or methacrylic acid per mole of OH groups of the alcohols to be esterified.

The esterification is preferably carried out with an esterification catalyst, for example sulfuric acid or p-toluenesulfonic acid, in amounts of preferably from 0.1 to 3% by weight, based on the total weight of the components to be esterified.

To avoid any polymerization of the (meth)acrylic acid, it is customary to add polymerization inhibitors as well.

The esterification is carried out for example at 40°–120° C., preferably 70°–120° C., and particularly suitable entrainers for removing the water of reaction are aliphatic or cycloaliphatic or aromatic hydrocarbons or mixtures thereof, especially those having a boiling range from 40° to 120° C., preferably from 70° to 120° C.

Suitable aliphatic hydrocarbons include for example hexane and its isomers, cyclohexane, methylcyclohexane, but especially higher boiling hydrocarbon mixtures which may also comprise higher or lower boiling hydrocarbons. Toluene is particularly preferred. The amount of hydrocarbon added is absolutely uncritical; depending on the apparatus used to carry out the esterification, the amount added can vary within the range from 0.05 to 2 times the amount of the reaction mixture of (meth)acrylic acid and alcohol. A mixing ratio of from 1:0.1 to 1:0.5 of esterification mixture to hydrocarbon is advantageous.

The hydrocarbon solvent is used as entrainer in the esterification to remove the water formed. For the purposes of the present invention the esterification thus has to be carried out under apparatus conditions where such a removal of the water of reaction is possible. It is customary to use the customary water separators. The course of the reaction can be monitored by determining the acid number, for example.

In general, the esterification is discontinued as soon as an acid number of from 40 to 120 mg of KOH per 1 g of reaction mixture (sum of reaction product and remaining starting components, without solvent, water) is reached. The acid number is determined by the method of DIN 53402.

Volatiles, such as organic solvents or water or else, as the case may be, part of the (meth)acrylic acid, can be removed from the reaction mixture by vacuum distillation, for example. For the removal of the remaining acrylic acid or methacrylic acid there are various prior art processes which are each very complicated and associated with disadvantages (see introduction).

In the process of this invention, at least one amino compound having at least one primary, secondary or tertiary amino group is added when the acid number is at least 5 mg of KOH per 1 g of reaction mixture, preferably within the range from 5 to 120 mg of KOH, particularly preferably within the range from 10 to 80 and most preferably from 15 to 40 mg of KOH per 1 g of reaction mixture.

The amount of amino compound(s) added is preferably determined in such a way that the molar number of the primary, secondary and/or tertiary amino groups at least corresponds to the number of moles of the acrylic or methacrylic acid still present. Preferably, the ratio of the number of moles of the amino groups to the number of moles of (meth)acrylic acid is within the range from 1:1 to 10:1, particularly preferably from 1:1 to 5:1.

The amino compounds added combine with the (meth) acrylic acid to form salts which, unlike the free (meth) acrylic acid, are odorless. When primary or secondary amino groups are present, a Michael addition between these amino groups and the acrylic acid or the acrylic esters obtained will occur as well to some extent.

Preferred amino compounds are those having a molecular weight below 2000, preferably below 1000, particularly preferably below 500, g/mol.

Particular preference is given to amino compounds having a dissociation constant $pK_b<3.5$, particularly preferably <3 (in water at 25° C.). In the case of multistage dissociation, the specified value applies to the 1st dissociation stage.

Particularly preferred amino compounds having primary amino groups are $C_2$–$C_{10}$-alkylamines substituted by a $C_1$–$C_{10}$-alkoxy group on the alkyl radical, for example 3-methoxypropylamine, 3-ethoxypropylamine and 2-ethylhexoxy-3-propylamine.

The primary amino groups, ie. with one substituent, preferably contain a hetero atom, especially an oxygen atom, in the substituent. Preferably the hetero atom is disposed γ or δ relative to the nitrogen atom; that is, nitrogen atom and hetero atom are linked via 2 or 3 carbon atoms.

Particularly preferred amino compounds having secondary amino groups are

N-ethylisopropanolamine and

N-ethylcyclohexylamine.

In the secondary amino groups (ie. with 2 substituents), the two substituents are preferably not the same. More particularly, at least one of the substituents contains a hetero atom as described above for the primary amino groups.

Particularly preferred amino compounds having tertiary amino groups are

N,N-dimethylisopropylamine,

N-hydroxyethylmorpholine,

N-hydroxyethyl-N,N-dibutylamine and

N-methyl-N,N-diisopropanolamine.

In the tertiary amino groups (ie. with 3 substituents), preferably at least 2 substituents are not the same. More particularly, at least one of the substituents contains a hetero atom as described above for the primary amino groups.

Particularly preferred amino compounds having primary and tertiary amino groups are N,N-diethyl- 4-aminopentylamine and N,N-diethylamino- 3-propylamine.

The above remarks apply to the nature of the primary and tertiary amino groups in these amino compounds.

The addition of amino compounds to organic mixtures comprising acids, for example acrylic acid, methacrylic acid or else, for example, acidic esterification catalysts, may in certain circumstances cause the resulting salts to crystallize out of organic media. In the case of the foregoing preferred and particularly preferred amino compounds, no crystallization of salts was observed following addition to the (meth)acrylic esters comprising the above-mentioned residual quantity of acrylic acid or methacrylic acid and also, as the case may be, additional residual quantities of the esterification catalyst. The (meth)acrylic esters were storage-stable over prolonged periods ( 3 months, for example) in that no cloudiness developed.

The (meth)acrylic esters obtainable by the processes of this invention can be used alone, ie. as sole radiation-curable compounds, or together with other radiation-curable compounds, in radiation-curable compositions. Preferred radiation-curable compositions comprise from 10 to 100% by weight, particularly preferably from 50 to 100% by weight, most preferably from 70 to 100% by weight of the (meth)acrylic esters of this invention, based on the total amount of the radiation-curable compounds.

The radiation-curable compositions can be used as or in coating compositions, for example paints, printing inks or adhesives, as printing plates, as moldings, for preparing photoresists, in stereolithography or as casting composition, for example for optical lenses.

Additives, for example crosslinkers, thickeners, flow control agents or fillers pigments etc., can be added for use as or in radiation-curable compositions.

The radiation-curable (meth)acrylic esters or compositions can be cured thermally, preferably by means of high-energy radiation such as UV light or electron beams.

For radiation-curing by UV light it is customary to add photoinitiators.

Examples of suitable photoinitiators include benzophenone and derivatives thereof, for example alkylbenzophenones, halomethylated benzophenones, Michler's ketone, and also benzoin and benzoin ethers such as ethyl benzoin ether, benzil ketals such as benzil dimethyl ketal, acetophenone derivatives, for example hydroxy-2-methylphenyl-1-propanone and hydroxycyclohexyl phenyl ketone, anthraquinone and its derivatives, such as methylanthraquinone, and especially arylphosphine oxides, for example Lucirin® TPO (2,4,6-trimethylbenzoyldiphenylphosphine oxide).

The photoinitiators, which depending on the application of the compositions of the invention are used in amounts within the range from 0.1 to 15% by weight, preferably from 1 to 10% by weight, based on the polymerizable components, can be used as individual substance or else, because of frequent advantageous synergistic effects, in combination with one another.

The radiation-curable (meth)acrylic esters possess good application properties, for example hardness, flexibility, chemical resistance and especially an improved adhesion to a wide variety of substrates, for example to glass.

EXAMPLES

1. Example with a primary amine: 3-methoxypropylamine

In a reaction vessel 622 g of an ethoxylated trihydric alcohol (trimethylolpropane) are combined with 2 g of sulfuric acid and 529 g of acrylic acid (freshly distilled), then 384 g of an entrainer (cyclohexane) are introduced, and the resulting mixture is refluxed under a water separator with vigorous stirring. After 6–8 hours the theoretical amount of water has been separated off and the reaction batch is freed from the azeotropic entrainer by distillation under reduced pressure. The reaction vessel then contains 1020.5 g of an oligomeric triacrylate comprising free acrylic acid. Following determination of the free acrylic acid content by titrating the acid number (acid number =15.7), 51.3 g (twice the stoichiometric amount) are added of 3-methoxypropylamine dropwise. After the reaction mixture has been cooled down, the acrylate is discharged and used directly for radiation curing of coating compositions on wood and paper. Characteristic values: viscosity 285 mPas, iodine color number: 1–2, odorless, storage-stable at 60° C. for 3 months.

2. Example with secondary amine: N-ethyl-N-isopropanolamine

In a reaction vessel 622 g of an ethoxylated trihydric alcohol (trimethylolpropane) are combined with 2 g of sulfuric acid and 529 g of acrylic acid (freshly distilled), then 384 g of cyclohexane are introduced, and the resulting mixture is refluxed under a water separator with vigorous stirring. After 6–8 hours the theoretical amount of water has been separated off and the reaction batch is freed from the azeotropic entrainer by distillation under reduced pressure. The reaction vessel then contains 1020.5 g of an oligomeric triacrylate comprising free acrylic acid. Following determination of the free acrylic acid content by titrating the acid number (acid number =15.7), 46.3 g (twice the stoichiometric amount) are added of N-ethyl-N-isopropanolamine dropwise. After the reaction mixture has been cooled down, the acrylate is discharged and used directly for radiation curing of coating compositions on wood and paper. Characteristic values: viscosity 130 mPas, iodine color number: 1–2, odorless, storage-stable at 60° C. for 3 months.

3. Example with a tertiary amine: dimethylisopropylamine

In a reaction vessel 622 g of an ethoxylated trihydric alcohol (trimethylolpropane) are combined with 2 g of sulfuric acid and 529 g of acrylic acid (freshly distilled), then 384 g of cyclohexane are introduced, and the resulting mixture is refluxed under a water separator with vigorous stirring. After 6–8 hours the theoretical amount of water has been separated off and the reaction batch is freed from the azeotropic entrainer by distillation under reduced pressure. The reaction vessel then contains 1020.5 g of an oligomeric triacrylate comprising free acrylic acid. Following determination of the free acrylic acid content by titrating the acid number (acid number =15.7), 31.7 g ( 1.2 times the stoichiometric amount) are added of dimethylisopropylamine dropwise. After the reaction mixture has been cooled down, the acrylate is discharged and used directly for radiation curing of coating compositions on wood and paper. Characteristic values: viscosity 285 mpas, iodine color number: 1–2, odorless, storage-stable at 60° C. for 3 months.

Application tests

The resulting (meth)acrylic esters of Examples 1 to 3 were each admixed with 3% by weight of Irgacure® as photoinitiator. The (meth)acrylic esters were drawn down with a box doctor (layer thickness 50 μm) and irradiated with two 80 watt UV lamps.

Reactivity

The samples are irradiated on a conveyor belt passing underneath the UV lamps. A measure of the reactivity is the speed (in m/min) of the conveyor belt at which the samples cure to form mar-resistant coatings.

Pendulum damping and Erichsen indentation

Pendulum damping was determined in accordance with DIN 53157 (reported in seconds), which is a measure of the hardness of a coating, and the Erichsen indentation was determined in accordance with DIN ISO 1520 (reported in millimeters), which is a measure of the flexibility, elasticity of a coating.

Chemical resistance

The chemical resistance was determined in accordance with DIN 68861 and is reported in ratings from 0 to 5, low values denoting good chemical resistance.

TABLE

| | Results of tests | | | |
|---|---|---|---|---|
| Example | Pendulum hardness | Erichsen indentation | Chemical resistance | Reactivity |
| 1 | 78 | 3.85 | 0.85 | 25 |
| 2 | 106 | 2.9 | 0.85 | 15 |
| 3 | 81 | 3.85 | 0.85 | 15 |

We claim:

1. A process for preparing (meth)acrylic esters by esterifying (meth)acrylic acid with monohydric or polyhydric alcohols, which consists essentially of adding to the reaction mixture still comprising (meth)acrylic acid corresponding to an acid number of at least 5 mg of KOH per 1 g of reaction mixture at least one amino compound having at least one primary, secondary or tertiary amino group to form a salt therewith.

2. A process as claimed in claim 1, wherein the number of the primary, secondary and tertiary amino groups of the amino compounds is at least equimolar to the (meth)acrylic acid.

3. A process as claimed in claim 1, wherein the amino compound comprises $C_2$–$C_{10}$-alkylamines substituted by a $C_1$–$C_{10}$-alkoxy group on the alkyl radical, or N-ethylisopropanolamine, N-ethylcyclohexylamine, N,N-dimethylisopropanolamine, N-hydroxyethylmorpholine, N-hydroxyethyl-, N-butyl-butylamine, N-methyl-N-isopropanol-isopropanolamine, N,N-diethyl-4-aminopentylamine, N,N-diethyl-3-aminopropylamine.

4. A method of coating, comprising applying to a substrate the radiation-curable composition obtained by the process as claimed in claim 1.

5. The method as claimed in claim 4, wherein said composition is radiation-cured.

6. A process as claimed in claim 1, consisting of adding to the reaction mixture said at least one amino compound.

* * * * *

UNITED STATES PATENT AND TRADEMARK OFFICE
CERTIFICATE OF CORRECTION

PATENT NO. : 5,821,383
DATED : October 13, 1998
INVENTOR(S) : Lukas HAUSSLING, et al.

It is certified that error appears in the above-identified patent and that said Letters Patent is hereby corrected as shown below:

On the title page, Item [73], the assignee, is incorrect. It should read:

--BASF Aktiengesellschaft, Germany--

Signed and Sealed this

Eighteenth Day of May, 1999

Attest:

Attesting Officer

Q. TODD DICKINSON

Acting Commissioner of Patents and Trademarks